United States Patent [19]

Yamada et al.

[11] 4,456,580

[45] Jun. 26, 1984

[54] AUTOMATIC APPARATUS FOR ANALYZING METALS

[75] Inventors: Takeshi Yamada; Hideki Ohashi; Masahiro Tanimoto, all of Kyoto, Japan

[73] Assignee: Horiba, Ltd., Kyoto, Japan

[21] Appl. No.: 349,664

[22] Filed: Feb. 17, 1982

[30] Foreign Application Priority Data

Sep. 17, 1981 [JP] Japan .................................. 56-148412

[51] Int. Cl.³ .......................... G01N 1/00; G01N 35/04
[52] U.S. Cl. .......................................... 422/63; 422/65; 422/67; 422/78; 422/102; 422/104; 422/240; 422/80; 436/115; 436/123; 436/145; 436/155; 177/50; 177/52
[58] Field of Search .................................. 422/63–67, 422/78, 102, 104, 80, 115, 123, 145; 436/155; 177/50, 52, 150, 54

[56] References Cited

U.S. PATENT DOCUMENTS

| | | | |
|---|---|---|---|
| 4,224,032 | 9/1980 | Glover et al. | 422/65 |
| 4,238,450 | 12/1980 | Bredeweg et al. | 422/63 |
| 4,248,315 | 2/1981 | Falinower | 422/68 |
| 4,301,116 | 11/1981 | Ida et al. | 422/65 |
| 4,338,279 | 7/1982 | Orimo et al. | 422/67 |

Primary Examiner—Michael S. Marcus
Attorney, Agent, or Firm—Wenderoth, Lind & Ponack

[57] ABSTRACT

An automatic apparatus for loading and feeding crucibles to and removing crucibles from a combustion furnace in which metals are burned for analyzing them. The apparatus has a part for automatically transporting crucibles to a sample weighing position one by one, a sample weighing device at the sample weighing position, and a supply device for placing the desired quantity of metal to be analyzed into crucibles at the sample weighing position. A storage device for automatically storing crucibles containing samples therein extends from the sample weighing position, and a device takes crucibles out of the storage device one by one and a further device automatically takes the crucibles from said taking out device and introduces them into a combustion furnace and removes the crucibles from the combustion furnace. A device then automatically dumps the crucibles removed from the combustion furnace after the completion of analysis. The storage device has a carrying trough for holding a line of crucibles, a stop at the downstream end of the carrying trough and movable into and out of engagement with the crucible at the downstream end of the carrying trough, and a pusher for pushing crucibles from the sample weighing position along the carrying trough and having a device for discontinuing the pushing action of said pusher when a crucible being pushed engages the stop or a crucible preceeding a crucible stopped by the stop.

11 Claims, 8 Drawing Figures

AUTOMATIC APPARATUS FOR ANALYZING METALS

The present invention relates to an automatic apparatus for analyzing metals, for example for carbon, surfur, hydrogen or oxygen contained therein, by burning metal samples placed in a crucible in a combustion furnace.

BACKGROUND OF THE INVENTION AND PRIOR ART

When such apparatus is operated manually, organic substances stuck to the crucible from the hands of the operator if he grasps the crucible with his hands lead to errors in analysis. Accordingly, the operation is made more difficult since the operator must grasp the crucible with pincers.

To avoid this, one apparatus of this type, for example the apparatus disclosed in U.S. Pat. No. 4,238,450, has been partly automated. However, only the introduction of a crucible into a combustion furnace and the discharge of the crucible from the combustion furnace is automated.

OBJECT AND BRIEF SUMMARY OF THE INVENTION

It is an object of the present invention to provide an automatic apparatus for analyzing metals which can eliminate the above described disadvantages incidental to the conventional apparatus and the substantially full automation can be attained by means of simple mechanisms which thus enable operation with fewer errors.

This object is achieved according to the present invention by the provision of an automatic apparatus for loading and feeding crucibles to and removing crucibles from a combustion furnace in which metals are burned for analyzing them, said apparatus comprising:

means for automatically transporting crucibles to a sample weighing position one by one;

a sample weighing means at said sample weighing position;

means for placing the desired quantity of metal to be analyzed into crucibles at said sample weighing position;

a storage means for automatically storing crucibles containing samples therein;

means for taking crucibles out of said storage means one by one;

means for automatically taking crucibles from said taking out means and introducing them into a combustion furnace and removing said crucibles from the combustion furnace; and means for automatically dumping crucibles removed from the combustion furnace after the completion of analysis, said storage means having a carrying trough for holding a line of crucibles, a stop at the downstream end of said carrying trough and moveable into and out of engagement with the crucible at the downstream end of said carrying trough, and a pusher for pushing crucibles from said sample weighing position along said carrying trough and having means for discontinuing the pushing action of said pusher when a crucible being pushed engages said stop or a crucible preceeding a crucible stopped by said stop.

DETAILED DESCRIPTION OF THE INVENTION

Figures 1, 2:
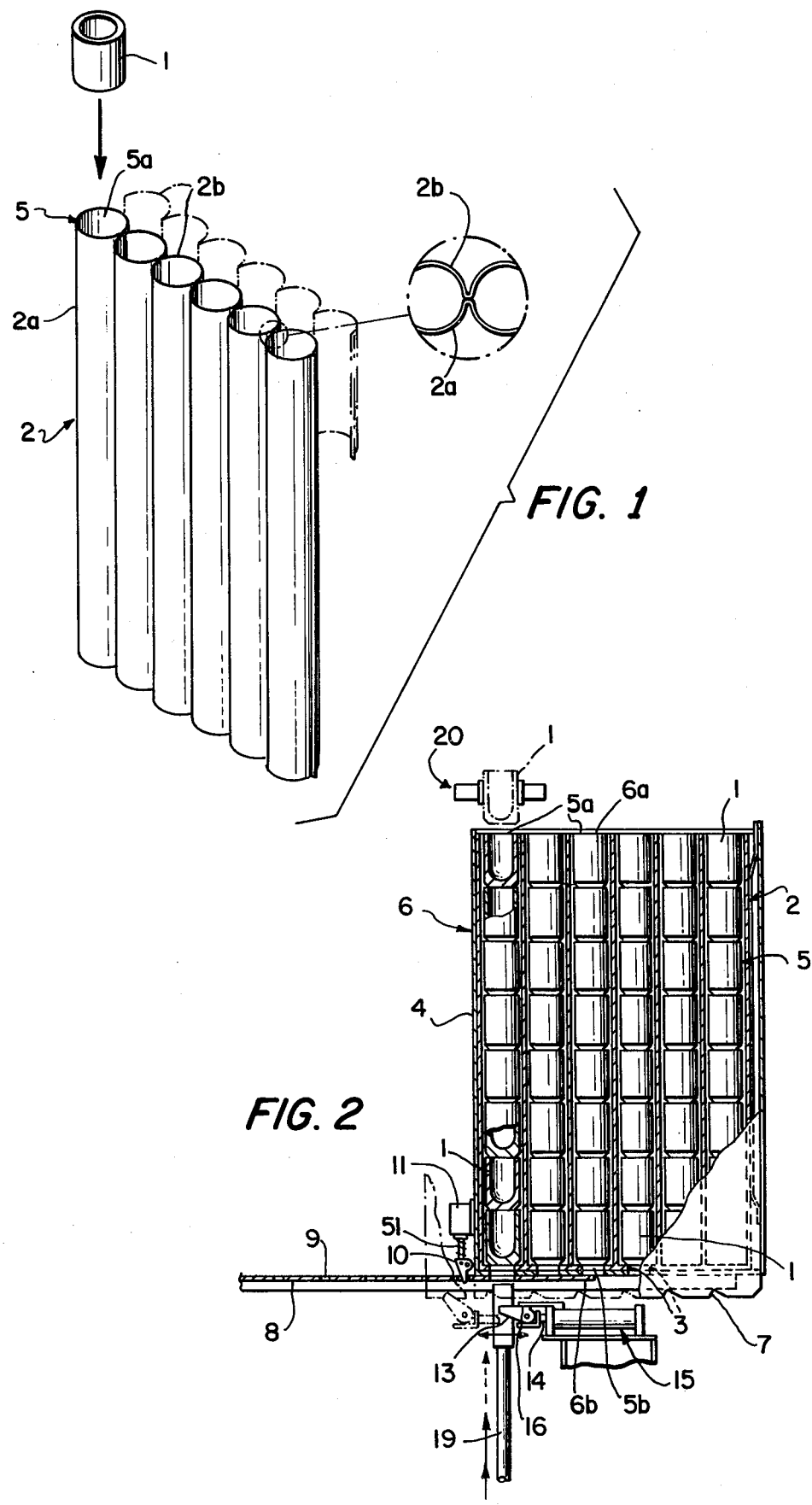
FIG. 1 is a perspective view of crucible holding cassette forming part of an automatic apparatus for analyzing metals according to the present invention.
FIG. 2 is a vertical cross section of the part of the apparatus shown in FIG. 1.

FIG. 1 shows a cassette 2 for holding ceramic crucibles 1 during metal analysis. In this embodiment, said cassette 2 is constructed from two halves 2a and 2b which are in the form of side by side half tubes which when joined to the other half by spot welding form side by side tubes 5 each capable of holding a plurality of crucibles 1 stacked one on top of the other. As shown in FIG. 2, at the bottom of each tube is an engaging member 3 against which the lowermost crucible 1 abuts, and a guide member 4 is provided for guiding the rise (described later) of the crucibles 1. Each of the plurality of cylindrical crucible receiving tubes 5, six tubes in this preferred embodiment, receive a plurality of eight said crucibles 1.

The cassette 2 is made of a material which does not contain any of the components for which the analysis is to be conducted, such as aluminium, nickel, chromium and the like, or at most contains only a small amount thereof. Plastic materials such as ABS resin, having portions contacting a crucible, for example said engaging member 3, said guide member 4 and the like, are coated with a material such as aluminium, nickel, chromium or the like.

Figure 3:
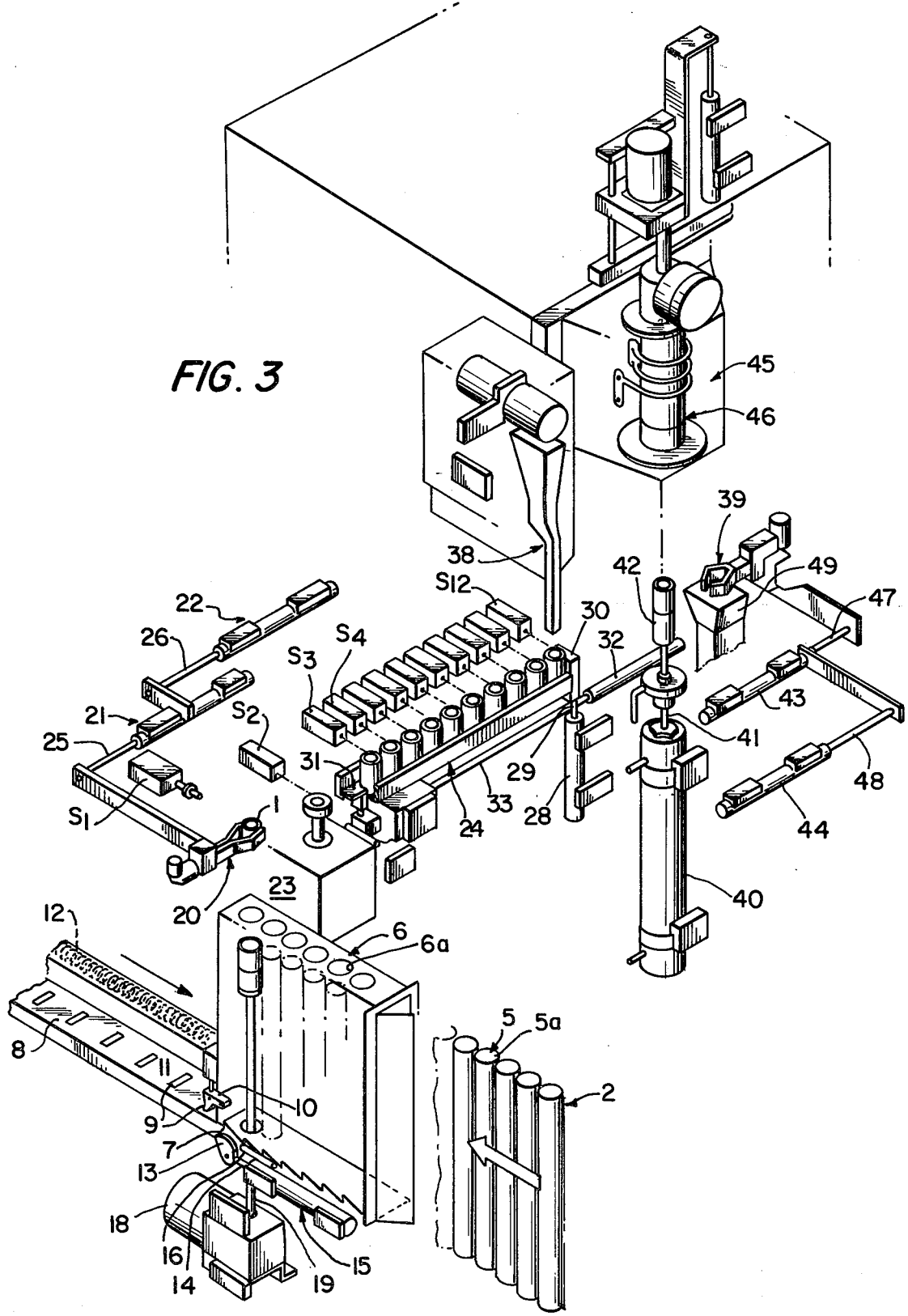
FIG. 3 is an exploded perspective view of the entire apparatus.

The cassette 2 having the plurality of crucibles 1 therein is inserted laterally into a cassette case 6 as shown in FIGS. 2 and 3. Said cassette case 6 is provided with openings 6a and 6b in the top and bottom positions corresponding the upper and lower openings 5a and 5b of said crucible receiving tubes 5, a plurality of engaging notches 7 in the lower surface thereof. An engaging latch 10 on one side thereof is engaged in one of a plurality of small holes 9 in a transfer table 8 and is urged downwardly by a spring 51, and a solenoid 11 is connected to said latch 10 for disengaging it.

A spring 12 is engaged with said cassette case 6 for pushing said cassette to a first position as shown in FIG. 3. A driving means 15 such as a piston-cylinder device is provided for moving said cassette case 6 against the force of said spring 12. The piston rod 14 thereof is provided with a latch 13 for engaging in said engaging notches 7. Said latch 13 normally projects upwardly to engage in said engaging notches 7 due to the force of a spring (not shown) when the rod 14 moves leftwardly, as shown by phantom lines in FIG. 2, and said latch 13 is pushed down by a pushing member 16 mounted on said piston-cylinder means 15 so as to be disengaged from said engaging notches 7 when said rod moves rightwardly, as shown in full lines in FIG. 2.

There is also provided a lifting means 17 for lifting said crucibles 1 in said cassette 2, a rod 19 which is driven by a motor 18 so as to move upwardly inside a cylindrical receiving tube 5 of said cassette 2. The upper free end of said rod 19 engages the bottom of a stack of crucibles in a receiving tube 5 and urges the crucibles out of said cassette 2 one after another beginning with the uppermost crucible. Further, in this preferred embodiment, each crucible 1 which reaches the point above the top of the case 6 is detected by an optical sensor $S_1$ which generates a detection signal which is supplied to said lifting means to stop the movement of rod 19. Alternatively said rod 19 may be moved upwardly intermittently a distance equal to the height of one crucible.

A first robot 20 is provided for transferring the crucible 1 which has been moved to the position above the case 6 by means of lifting means 17, to a balance 23, which is one example of an apparatus for measuring a characteristic of a sample to be analyzed, and further transferring said crucible 1 into which a definite quantity of a sample has been charged in said balance 23, to a storage means 24. The robot includes driving means in the form of piston-cylinder devices 21 and 22 having piston rods 25 and 26 respectively.

In operation, cassette 2 which has a plurality of crucibles 1 therein, is inserted into said cassette case 6 positioned in the first position shown in FIG. 3, and then the crucibles 1 are lifted upwardly out of the case 6 one after another by said rod 19. Each lifted crucible is grasped by the first robot 20 and transferred to said balance 23 by the movement of the rod 25 of said cylinder 21. An operator can read the weight of a sample by, for example, pushing an input key (not shown), which causes automatic read out of the weight after placing the desired quantity of metallic sample in said crucible 1. Alternatively, this sample-weighing may be automated. After the weighing of the sample is completed, the operator actuates the apparatus to cause said rod 25 of said cylinder 21 and said rod 26 of said cylinder 22 to move simultaneously to place said crucible 1 on the rear end of a carrying trough 27 (described later) of said storage means 24.

When all of the crucibles 1 arranged in the first receiving tube of said cassette 2 have been removed by repeating the above described actions, said motor 18 is reversed to lower said rod 19 of said lifter 17 out of said cassette 2, and said engaging latch 10 is disengaged from said hole 9 by operation of said solenoid 11. The rod 14 of said driving means 15 moved leftward, and said latch 13 is engaged with said engaging notch 7 for moving said cassette case 6 leftward one pitch against the force of said spring 12. Said solenoid 11 is deenergized and said engaging latch 10 then engages in the next narrow hole 9 to the left in FIGS. 2 and 3, whereby said cassette case 6 is fixed at the next position. The crucibles 1 in the next receiving tube 5 are then lifted out one after another in the same way as above described. After all of said crucibles 1 are removed from the sixth receiving tube 5, said engaging latch 10 is disengaged from the corresponding narrow hole 9 by the action of said solenoid 11, and said cassette case 6 is returned to the first position by the action of said spring 12.

Figure 4:
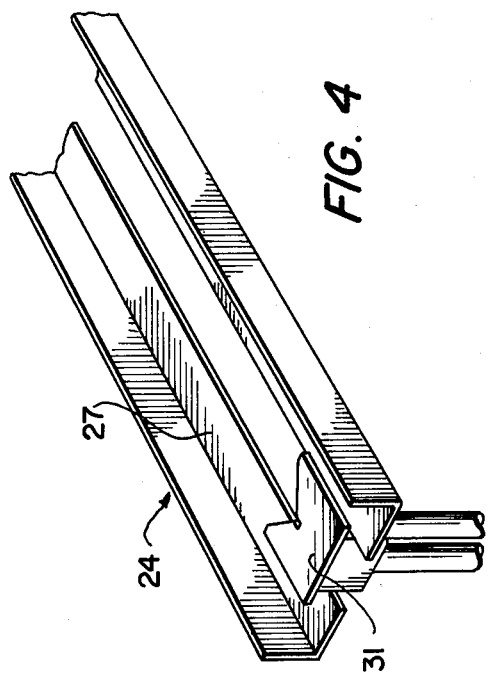
FIG. 4 is an enlarged perspective view of one of the main parts of the apparatus according to the present invention.
Figure 5:
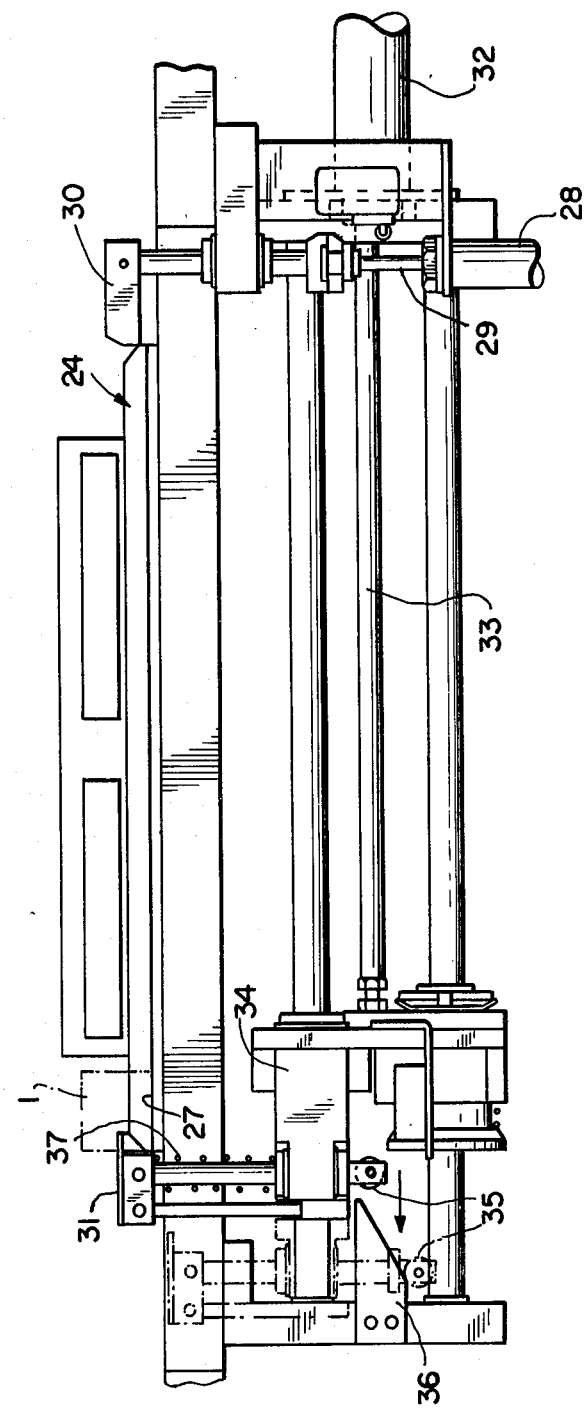
FIG. 5 is a partial side view of the apparatus according to the present invention.

Referring now to said storage means 24, said storage means 24 consists of said carrying trough 27, which has two spaced parallel side rails as shown in detail in FIGS. 4 and 5, for carrying said crucibles and storing them in line; a stop 30, which is moved into and out of the path of the crucibles 1 on table by the reciprocating movements of a rod 29 of a piston-cylinder device 28, engaging said crucible 1 at the end of said carrying table 27 remote from said balance 23; and a pusher 21 movable between said rails for pushing a crucible 1 which has been transferred from said balance 23 along said trough 27.

Said pusher 31 is supported on a bracket 34 mounted at the free end of the piston rod 33 of a piston-cylinder mechanism 32 and is slidable upwards and downwards on bracket 34. It is shown located at the lifted position in full lines in FIG. 5 and is normally urged to the lifted position by the action of a spring 37. Crucibles 1 are pushed along said carrying trough 27 by said pusher 31 by movement of said rod 33 to the right in FIG. 5, while the return movement of said rod 33 and contacting of the guide roller 35 with a cam member 36 causes the descent of said pusher 31 against the action of a spring 37 to a position at which said pusher 31 moves beneath said crucibles 1 in said trough 27.

When a crucible 1 transferred by said pusher 31 contacts with said stop 30 or a crucible ahead of the crucible being blocked by said stop 30 and the pusher 31 detects the reaction force, pressure within cylinder 32 increases.

When this increase of the pressure is transmitted to a reversing valve (not shown) the reversing valve is changed and rod 33 moves in the reverse direction.

Accordingly, said crucibles 1 transferred into said carrying trough 27 by means of said first robot 20 after a sample therein has been weighed are stored in the trough 27 one after another in a line without gaps therebetween. An automatic apparatus 38 is provided for feeding a combustion-accelerating agent, for example tungsten, in the desired quantity into the crucible 1 at the front end of the said storage means 24.

Various kinds of well known apparatus can be used as the above automatic apparatus 38 for feeding a combustion-accelerating agent. A second robot 39 is provided which includes piston-cylinder device 43 and 44 similar to said first robot 20, for transporting a crucible containing the charge and the combustion-accelerating agent to a crucible table 42 mounted on the free end of a rod 41 of a piston-cylinder mechanism 40 and transporting said crucible from said crucible table 42 to a waste chute 49 after the analysis is completed. Positioned above the mechanism 40 is a combustion furnace 46 including a gas extracting means 45 for recovering gases produced during combustion of the material in a crucible and carrying them to an analyzing means (not shown) by means of a carrier gas.

In operation, the crucible at the front end of said storage means 24 is grasped by said second robot 39 while the rods 47 and 48 of both said piston-cylinder mechanisms 43 and 44 are retracted, and the crucible is moved and placed on said crucible table 42 by extending only one of the rods, such as the rod 48, after which the crucible 1 is released. Then the rod 41 of the mechanism 40 is extended to raise the crucible 1 into said combustion furnace 46 where the sample contained in said crucible 1 is burnt. Elements, for example carbon, sulfur and the like, contained in the sample are discharged in the form of $CO_2$, $SO_2$ and the like, respectively and are carried to the analyzing portion (not shown) by carrier gas to be analyzed. Said analyzing portion is provided, for example, with an infrared absorption analyzer for analyzing for carbon or sulfur, and with a thermal conductivity type analyzer for analyzing for nitrogen, hydrogen or oxygen. After the analysis is completed, said rod 41 is retracted to move the crucible 1 out of the combustion furnace 46 and then the inside of said combustion furnace 46 is cleaned by a cleaning device (not shown). Then said crucible 1 is grasped by said second robot 39, the other rod 47 is extended to transport said crucible 1 to a position just above the waste chute 49 where the crucible 1 is released from said second robot 39 and the crucible 1 is dumped.

As soon as the crucible 1 at the front end of said carrying trough 27 is removed, said stop 30 and said pusher 31 act to move the row of crucibles 1 ahead a distance corresponding to one crucible in order to move a new crucible to the front position.

In addition, the apparatus of the present invention is provided with a switch (not shown) which stops said second robot 39 when said switch is in the OFF-position. Also it is possible to store the crucibles 1 in said trough 27 while said switch is in the OFF-position and carry out an operation of said analyzing portion thereafter without need of human assistance by switching ON said switch at the point when said trough 27 is completely filled with crucibles 1.

Optical sensors $S_2$–$S_{12}$ are provided for sensing the presence of crucibles 1 on the balance 23 and in the trough 27.

The timing of the action of each of the parts of the apparatus is appropriately controlled by means of controlling devices (not shown) in this preferred embodiment of the present invention.

It is, of course, to be understood that the present invention is by no means limited to the specific construction shown in the drawings and described above, but can also comprise modifications within the scope of the appended claims.

Figure 6:
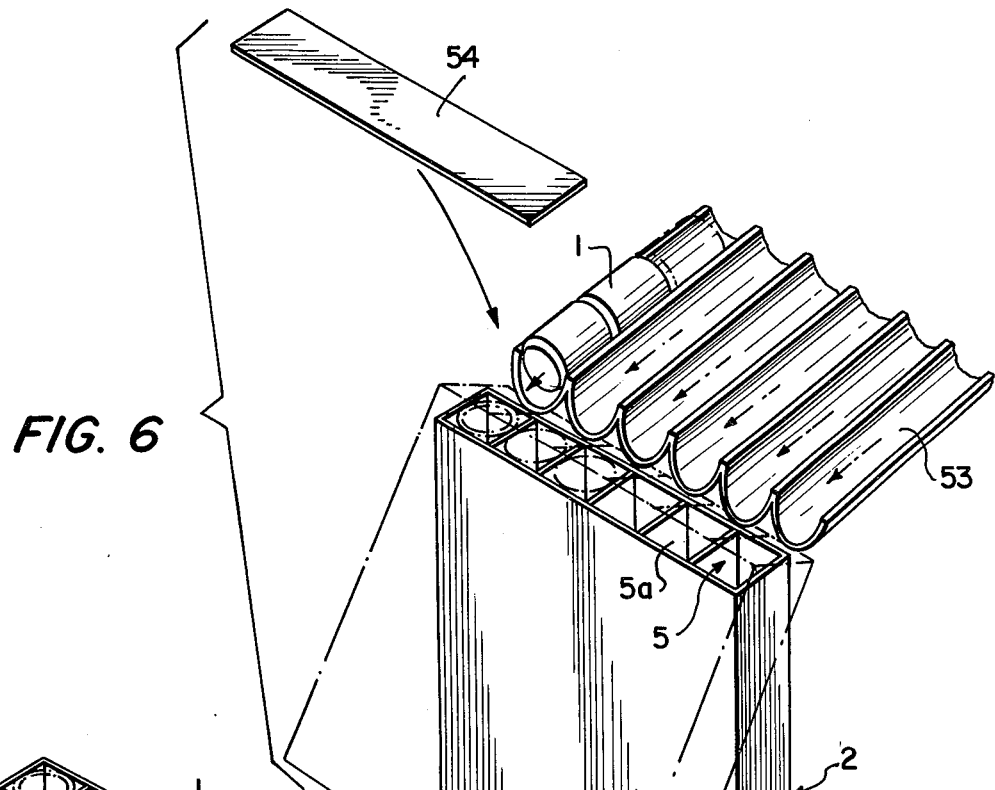
FIGS. 6, 7, 8 are the perspective views of modified forms of the crucible holding cassette according to the present invention.
Figure 7:
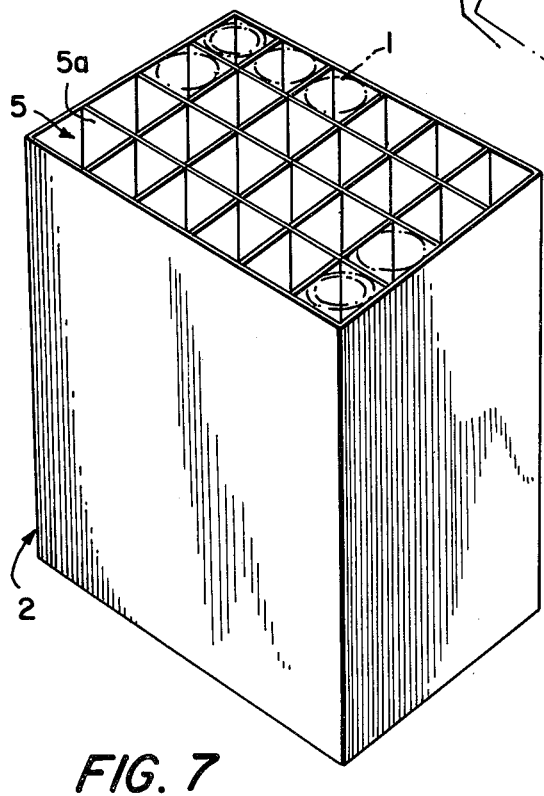

For example, the receiving tubes 5, the engaging members 3 and the guide members 4 in said cassette 2 can be modified for receiving crucibles 1 of various shapes and constructions. Rectangular cross-section receiving tubes, for example as shown in FIG. 6, can be used for receiving crucibles 1 instead of cylindrical receiving tubes as in the above described embodiment. Furthermore, a plurality of lines of crucible receiving tubes 5 may be provided in the cassette as shown in FIG. 7.

Figure 8:
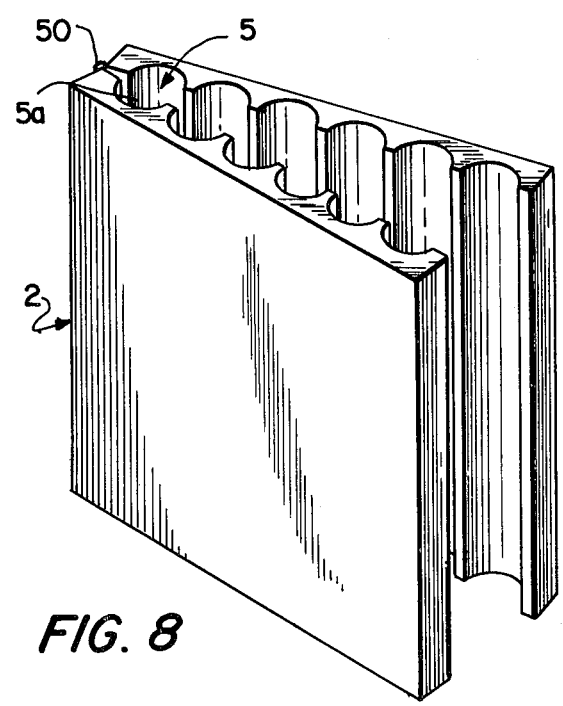

The halves of the cassette 2 for holding the crucibles 1 can be connected by a hinge 50 so as to be freely opened and closed as shown in FIG. 8, in order to make the insertion of said crucibles 1 easy. An appropriate locking mechanism should be provided for holding the halves closed.

A plurality of crucibles can be loaded into the cassette 2 in a single operation by means of a chute 53 as shown in FIG. 6. A cap plate 54 can be provided as shown in FIG. 6 in order to prevent the crucibles 1 from projecting upwards above the top of the cassette during the transportation of the cassette.

The cassette 2 can be loaded in a vacuum so that harmful dust contained in the air, for example textile refuse and the like containing components to be measured, such as carbon, will not be stuck thereto.

It will be seen that there has thus been provided an apparatus for analyzing metals which is almost completely automated. It is not necessary for an operator to touch any crucible 1 throughout the operation, from taking the crucible 1 out of the cassette to the dumping of the crucible 1 after the completion of analysis. Thus a great amount of labor can be saved. In addition, the weighing of the sample and the combustion analysis of the sample are separately carried out and do not interfere with each other, because the storage means is arranged between the sample-weighing means and the means for introducing the crucibles 1 into the combustion fornace and taking the crucibles 1 out of the combustion furnace. The storage means consists of said carrying trough for transporting a plurality of crucibles and storing them in line, the stop at the downstream end of the trough for engaging with and disengaging from the crucible 1 at the end of said carrying trough, and the pusher for moving crucibles from the sample-weighing means along the carrying trough and stopping the pushing action when a crucible contacts the stop or a preceding crucible stopped by the action of said stop. Accordingly, the timing of sample-weighing is not limited by the progress of combustion analysis. For example, the samples can be weighed one after another and stored in said storage means regardless of the time required for analysis even when the time required for analysis in said combustion furnace is comparatively long in comparison with the time required for weighing samples, whereby the efficiency of the operation can be improved. Thus it is not necessary to coordinate the analysis operation requiring a long time with the weighing operations, which can be carried out in a short time one after another. The crucibles are arranged in a line in said carrying trough with no gaps therebetween, whereby the crucibles can be smoothly introduced into the combustion furnace by means of a simple mechanism.

Furthermore, as described in detail hereinbefore, the cassette, which holds the crucibles to be transported to said sample-weighing portion, and which consists of a plurality of cylindrical receiving tubes for receiving a plurality of crucibles stacked one above the other and each having the engaging member for engaging the lowermost crucible and the guide member for guiding the rise of the crucibles and the parts thereof which contact the crucibles being made of materials which do not include the components to be measured, or materials containing only a minute quantity of said components to be measured, makes it very easy to load crucibles therein and remove crucibles therefrom in comparison with a cassette packed in a bag made of, for example, aluminium foil. In particular, it is necessary only to use a simple means such as a rod to push the crucibles upwardly out of the receiving tubes one after another.

The crucibles can be very easily and automatically removed because said crucibles can be removed by a simple means, whereby the supplying of crucibles, which has heretofore hindered the automation of an apparatus for analyzing metals has been eliminated.

A comparatively large number of crucibles can be held in a comparatively small space, which is advantageous in respect of packaging, transportation and storage, because the cassette has a plurality of parallel receiving tubes for receiving the crucibles.

What is claimed is:

1. An automatic apparatus for loading and feeding crucibles to and removing crucibles from a combustion furnace in which metals are burned for analyzing them, said apparatus comprising:
   means for automatically transporting crucibles one at a time to a sample weighing position where they can have a sample placed therein;
   a sampling weighing means at said sample weighing position;

a storage means adjacent said weighing position for automatically storing crucibles containing samples therein, said storage means having a carrying trough for holding a line of crucibles and having an upstream end for receiving crucibles one by one from said weighing means, a stop at the downstream end of said carrying trough against which a crucible moved along said trough to said downstream end abuts for being blocked against further movement, said stop being movable into and out of engagement with the crucible at the downstream end of said carrying trough for permitting the crucible at the downstream end of said trough to be taken out of the trough, and a means for transporting crucibles along said trough consisting of a pusher reciprocally movable along said trough, pusher driving means for moving said pusher for pushing crucibles one at a time from said sample weighing position along said trough and having means for discontinuing the pushing action of said pusher when a crucible being pushed engages said stop or a crucible preceding a crucible which has been stopped by said stop;

means for taking crucibles out of said weighing position one at a time and placing them on said upstream end of said trough;

means adjacent the downstream end of said trough for taking crucibles out of the downstream end of said trough one by one;

means for automatically taking crucibles from said taking out means and introducing them into a combustion furnace and removing said crucibles from the combustion furnace; and means for automatically dumping crucibles removed from the combustion furnace after the completion of analysis.

2. An apparatus as claimed in claim 1, further comprising means positioned along said carrying trough for automatically introducing a quantity of combustion-accelerating agent into crucibles stored along said carrying trough.

3. An apparatus claimed in clalim 1 in which said pusher driving means comprises means for lowering the pusher when it reaches the upstream end of said trough at the end of a return movement of said pusher, and said means for taking said crucibles out of said weighing position comprises means for grasping said crucibles in said weighing station and moving them in a straight linear movement into the upstream end of said trough over said pusher means.

4. An apparatus as claimed in claim 1 in which said means for transporting crucibles to said sample weighing position comprises a cassette means having at least one crucible receiving tube capable of receiving a plurality of crucibles stacked one above the other, and an engaging member in the bottom of the tube for engaging with the lowermost crucible and supporting it in the receiving tube and a guide member for guiding the rise of the crucibles in said tube, and means for pushing crucibles one by one up out of said tube and carrying them one by one to the sample weighing position.

5. An apparatus as claimed in claim 4 in which said cassette means comprises a plurality of parallel crucible receiving tubes each being capable of receiving a plurality of crucibles stacked one above the other, at least the parts of said crucible receiving tubes contacting said crucibles being made of materials containing none of the components for which the analysis is being carried out or containing only a minute amount thereof, and each receiving tube having such an engaging member in the bottom thereof for engaging with the lowermost crucible and supporting it in the receiving tube and a guide member for guiding the rise of the crucibles in said tube.

6. An apparatus as claimed in claim 5 in which said crucible receiving tubes are side by side, and each consists of two tube halves, the one halves of said tubes being connected to each other to form one cassette half and the other halves of said tubes being connected to each other to form the other cassette half, and means for holding said cassette halves together.

7. An apparatus as claimed in claim 6 in which said means for holding the cassette halves together comprises welds between the halves of the respective tubes.

8. An apparatus as claimed in claim 4 in which the position to which the crucibles are pushed when they are pushed up out of said tube is level with said weighing position and said trough, and said means for carrying said crucibles from said position to said weighing station is movable in a straight linear movement from said position to said weighing station.

9. An apparatus as claimed in claim 5 further comprising a cassette case in which said cassette can be positioned, and means for automatically transporting said cassette case to a position at which said crucibles are taken out.

10. An apparatus as claimed in claim 5 in which the materials for which the analysis is to be carried out are carbon, sulfur, nitrogen, hydrogen and oxygen, and the material of said receiving tubes is a material taken from the group consisting of aluminum, nickel and chromium.

11. An apparatus as claimed in claim 6 in which one end of one cassette half is hinged to the other half, and said means for holding the cassette halves together comprises locking means for holding the other ends of the halves to each other.

* * * * *